United States Patent [19]

Catsimpoolas et al.

[11] Patent Number: 4,699,788

[45] Date of Patent: Oct. 13, 1987

[54] ANGIOGENIC FACTOR METHODS OF EXTRACTION AND METHOD FOR PRODUCING ANGIOGENESIS

[75] Inventors: Nicholas Catsimpoolas, Newton Centre; Harry S. Goldsmith, Boston, both of Mass.

[73] Assignee: Trustees of Boston University, Boston, Mass.

[21] Appl. No.: 642,624

[22] Filed: Aug. 20, 1984

[51] Int. Cl.$^4$ ............................................. A61K 35/38
[52] U.S. Cl. ...................................... 424/104; 424/95
[58] Field of Search ........................ 424/95, 104; 514/2

[56] References Cited

U.S. PATENT DOCUMENTS

| | | |
|---|---|---|
| 4,209,587 | 6/1980 | Tolbert et al. . |
| 4,210,718 | 7/1980 | Tolbert et al. . |
| 4,210,719 | 7/1980 | Tolbert et al. . |
| 4,217,412 | 8/1980 | Tolbert et al. . |
| 4,225,670 | 9/1980 | Tolbert et al. . |
| 4,229,531 | 10/1980 | Tolbert et al. . |
| 4,229,532 | 10/1980 | Tolbert et al. . |
| 4,268,629 | 5/1981 | Tolbert et al. . |
| 4,273,871 | 6/1981 | Tolbert et al. . |
| 4,529,590 | 7/1985 | LeVeen et al. ........................ 424/95 |

FOREIGN PATENT DOCUMENTS 0038511 10/1981 European Pat. Off. .
0095682 5/1983 European Pat. Off. .

OTHER PUBLICATIONS

Goldsmith et al–JAMA, vol. 252, No. 15, Oct. 19, 1984, pp. 2034–2036.
Rabinowitz et al–Biol. Abst., vol. 66.
Rabinowitz et al–Lipids, vol. 13, No. 5, (1978) pp. 317–322.

Primary Examiner—Sam Rosen
Attorney, Agent, or Firm—Felfe & Lynch

[57] ABSTRACT

A novel angiogenic composition obtained from the omentum is provided which acts as a potent and effective factor for blood perfusion enhancement and for the development of new blood vessels in an organized structural network in living tissues. The angiogenic composition is a lipid or lipids, essentially protein-free as extracted from the omentum using organic solvents. This composition can then be injected to target to a site where new blood vessel formation, or blood perfusion enhancement is required. This material can be used to heal various damaged tissues including bone and heart.

10 Claims, 11 Drawing Figures

72 Hours

Right Leg (B)  Left Leg (B)
232288 cpm    179831 cpm 29.6 % increase

6 Days (post op)

| RIGHT LEG | LEFT LEG |
|---|---|
| 159,000 cpm | 115,000 cpm |

38.2 % increase

Fig. 6.

Day 9

| RIGHT LEG | LEFT LEG |
|---|---|
| 95909 cpm | 57831 cpm |

65.8 % increase

ANGIOGENIC FACTOR METHODS OF EXTRACTION AND METHOD FOR PRODUCING ANGIOGENESIS

FIELD OF THE INVENTION

The present invention is directed generally towards compositions and methods for neovascularization in vivo in human and animal subjects, and is specifically concerned with angiogenic factors and methods for inducing angiogenesis using omentum derived preparations.

BACKGROUND OF THE INVENTION

Angiogenesis, the formation of new blood vessels and consequently increased blood circulation, and angiogenic factors, chemical compositions which initiate and mediate the formation of new blood vessels and circulation, have been a favorite area of research and investigation for many years. Much of this interest stems from the recognition that normal tissues in humans and animals can contain trace amounts of angiogenic compositions but do not show any angiogenic activity other than in the normal process of growth and development of tissues and organs. Angiogenesis and angiogenic factors have been observed, isolated, and purified mainly from pathological tissues of various kinds. For example, the significance of the interaction between the host vasculature and the survival and growth of solid malignant tumors has been recognized for well over a century [Virchow, R., *Die Krankhaften Geshwulste*, Hirshwald, Berlin, 1863; Thiersch, C., *Der Epithelialkrebs, Nanentlich Der Haut Mit Atlas*, Lipzig, 1865]. However, the first clear cut demonstration of the existence of a humoral, angiogenic factor was first demonstrated by Greenblatt and Schubik in their transfilter diffusion studies [*J. Natl. Cancer Inst.* 41:111–124(1968)]. Subsequent investigations of this tumor angiogenic factor has produced major differences and discrepancies in describing the composition and characteristics of the active factor [Folkman *et al., J. Exp. Med.* 133:275(1971); Weiss *et al., Br. J. Cancer* 40:493(1979); McAuslan *et al., Exp. Cell Res.* 119:181–190(1979); Fenselau *et al. J. Biol. Chem.* 256:9605–9611(1981)]. These investigations of the tumor angiogenic factor has led to concurrent research efforts by others for additional or similar chemical compositions. These include: the isolation of an angiogenic factor from synovial fluid resembling that from tumors having a molecular weight of approximately 200–300 daltons [Brown *et al., Lancet I*:682–685(1980)]. A proteinaceous angiogenic factor from human myocardial infarcts ranging from $300-1\times10^5$ daltons [Kumar *et al., Lancet II*:364–367(1983)]. Angiogenic factors in the vitreous fluid of humans with diabetic retinopathy and in the retinas of animals comprising proteins and polypeptides up to 70,000 daltons in molecular weight [Hill *et al., Experientia* 39:583–585(1983); D. Amore *et al., Proc. Natl. Acad. Sci. USA* 78:3068–3072(1981); Kissun *et al., Br. J. Ophth.* 66:165–169(1982)]. The isolation of an angiogenic protein from wound fluid having a molecular weight between 2,000 and 14,000 daltons [Banda *et al., Proc. Natl. Acad. Sci. USA* 79:7773–7777(1982)]. Protein complexes ranging from 100,000-200 daltons irom human amino-chorion and placenta which show angiogenic activity [Burgos, H., *Eur. J. Clin. Invest.* 13:289–296(1983)]. Poorly defined aqueous extracts which stimulate neovascularization from 3T3 adipocytes and human follicular fluid [Castellot *et al., Proc. Natl Acad. Sci. USA* 79:5597–5601(1982); Frederick *et al., Science* 224:389–390(1984)].

A method to isolate human tumor angiogenic factor (TAF) and factor from: non-tumors is described in a series of patents by Tolbert et al. [4,209,587 issued June 24, 1980; 4,217,412 issued Aug. 12, 1980; 4,225,670 issued Sept. 30, 1980; 4,229,531 and 4,229,532 issued Oct. 21, 1980; 4,268,629 issued May 19, 1981 and 4,273,871 issued June 16, 1981]. These relate only to a method of preparing crude factor from cell culture supernatants. 4,217,412 issued Aug. 12, 1980; 4,225,670 issued Sept. 30, 1980; 4,229,531 and 4,229,532 issued Oct. 21, 1980; 4,268,629 issued May 19, 1981 and 4,273,871 issued June 16, 1981). These relate only to a method for preparing crude factor from cell culture supernatants and are completely unrelated to the source and method of the angiogenesis factor claimed below.

The overall effect and conclusion drawn from these various research efforts may be summarized as follows: first, the angiogenic factor, regardless of source, has almost always been shown to be a protein, a protein complex, or a polypeptide in nature. Second, the true chemical structures of any of these compositions able to initiate or mediate angiogenesis has not yet been accurately described in detail; to the contrary, the variation and discrepancies of data from different groups of investigators regarding the molecular weight, between the multiplicity of compounds interacting to produce an angiogenic effect, and by the ability (or inability) to obtain a homogeneous purified preparation has been enormous. Lastly, the overwhelming majority of angiogenic factors previously reported have been required to be used as implanted pellets or preparations which slowly release the active factor over time in order to effect angiogenesis; this is believed due to the short life span, the high diffusibility and relatively low biological activity of the factors.

A totally different approach to angiogenesis is the surgical application of intact omentum to normal and traumatized tissues in the body by Harry S. Goldsmith and his coworkers [Goldsmith *et al., Arch. Surg.* 106:695–698(1973); Goldsmith *et al., Am. J. Surg.* 130:317–320(1975); Goldsmith *et al., Am. J. Surg.* 29:263–265(1975); Goldsmith *et al., Stroke* 9:224–229(1978); Goldsmith, H. S., *Rev. Surg.* 24:379–380(1967); Goldsmith, H. S., *Surgery* 88:732–736(1980); Goldsmith *et al.*, "Application Of Intact Omentum To The Normal And Traumatized Spinal Cord", in *Spinal Cord Reconstruction*, Raven Press, New York, 1983, pages 235-244]. These efforts demonstrated that the surgical attachment of intact omentum directly on the surfaces of the brain or spinal cord resulted in vascular anastomoses between the omentum and the other tissues sufficient to prevent infarction even in the presence of middle cerebral artery ligation. Gross examination and microscopic histological examination showed substantial development of vascular connections between the omentum in each of the tested tissues in the sacrificed animals. There is no description and no indication, however, in any of these reports regarding the particular factors, chemical or physiological, which cause the demonstrated neovascularization. Moreover, it is far from clear from any of the reported findings, that the omental factors have any similarity to those proteinaceous factors derived from tumors and the like as described herein previously.

SUMMARY OF THE INVENTION

An angiogenic factor is provided which comprises a biologically active lipid-like preparation obtained by extraction of a lipid fraction from an omentum homogenate using at least one organic solvent, the lipid-like fraction comprising oxygen, hydrogen and carbon and having molecular weight ions in the range of approximately 150-1,100 daltons. This angiogenic factor may be introduced into preselected sites in the body by injection or by surgical implantation and creates rapid and potent vascularization in a matter of days.

DETAILED DESCRIPTION OF THE DRAWING

The detailed description of the present invention may be more clearly and fully understood when taken in conjunction with the accompanying drawing, in which.

DETAILED DESCRIPTION OF THE PREFERRED EMBODIMENT

The present invention is a potent angiogenic composition and a method for producing angiogenesis which comprises a lipid preparation obtained from the omentum of animals which is the result of an extraction using at least one organic solvent. The angiogenic material obtained by this process from the omentum is abundant in supply, and contains at least one potent angiogenic factor which will cause the development of numerous neovascular connections in living tissue. The lipid preparation itself is heterogeneous in composition and has been found to contain at least five lipid-like subfractions which interact with one another to provide the most potent angiogenic effect. The active lipid-like molecules in the subfractions are compositions comprising oxygen, hydrogen, and carbon and have molecular weight in the range of approximately 150-1,100 daltons. Forming part of these active lipid-like molecules are aliphatic hydrocarbon compositions containing possibly not more than twenty carbon atoms per chain. For this reason, it is preferred that the extracted lipid preparation form comprise all the lipid subfractions as a heterogeneous mixture.

Figure 1:
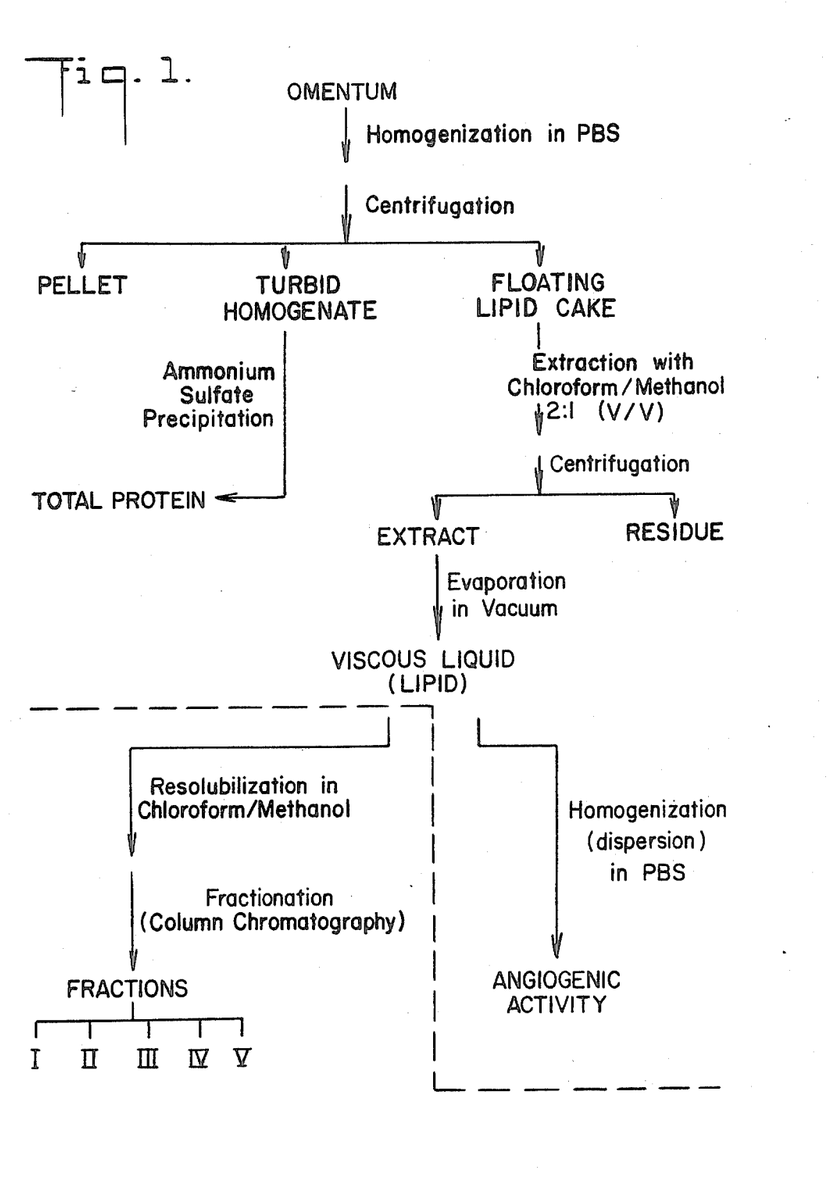
FIG. 1 is a schematic diagram illustrating the preferred method for extraction and fractionation of omental tissue.

The lipid-like angiogenic factor derived from the omentum is obtained according to the schematic diagram of omental tissue extraction and fractionation shown in FIG. 1.

The preferred method for procuring the angiogenic lipid-like preparation is as follows. Adult female cats weighing 2.4-3.2 kilograms (hereinafter "Kg") were anesthetized by an intramuscular injection of Ketamine at a preferred dosage of 7.0 milligrams per kilogram (hereinafter "mg/Kg"). Once anesthetized, a laparotomy was performed through a mid-line incision according to conventionally known surgical procedures. The omentum was surgically removed and placed into a sterile plastic bag held at 4° C. for immediate processing. Simultaneously, subcutaneous fat was also removed and treated in a manner identical to the omental tissue for use in our procedures as a non-omental lipid control. Using proper aseptic technique, the omentum was weighed, spread out onto a plastic surface and cut into individual pieces approximately four square centimeters in size using surgical scissors. These individual omental pieces, ranging in weight individually from 7 to 66 grams, were placed in a sterile Waring blender containing 300 milliliters (hereinafter "ml") of phosphate buffered saline (hereinafter "PBS") which was precooled to 4° C. The omental pieces were blended for five minutes at 20,500 rpm to yield an omental homogenate which was subsequently placed in sterile 250 ml plastic bottles and centrifuged at 1600 times gravity in a refrigerated centrifuge at 4° C. for twenty minutes. After centrifugation, three distinct and separable fractions were visible in the bottles: a pellet of mixed composition; a turbid homogenate containing substantially all the proteinaceous material, and a floating, cream colored, lipid cake. Each of these fractions was isolated individually.

The pellet of mixed composition was discarded completely. The turbid homogenate fraction was fully saturated (i.e. 100%) with aqueous ammonium sulfate which acted to precipitate the total protein in this fraction. Testing of the turbid homogenate fraction and the total protein precipitant (resuspended in PBS) revealed that neither of these preparations had any angiogenic activity whatsoever. Accordingly, it was shown that the angiogenic factor in the omentum does not comprise either a protein or a polypeptide to any meaningful degree.

The lipid fraction isolated as a floating lipid cake was composed of two distinct layers: an upper foamy composition and a more dense, compact layer which was darker in color than the upper. Each layer was evaluated and found to contain an active angiogenic factor in substantial quantity. For this reason, each of these lipid layers individually and in combination comprise the active lipid fraction per se of the present invention. The weight of the lipid cake comprising both layers was found to be approximately 93% of the total weight of the omentum from which it was derived and it is this lipid cake which is used to prepare the concentrated organic extract comprising the active angiogenic factor composition.

Active lipid-like fractions were extracted using the quantities and proportions of lipid cake given in Table I below.

TABLE I

| Exp. No. | Total Omentum* | Lipid Cake* | Portion of Lipid Cake Extracted* |
|---|---|---|---|
| 1 | 31.2 | NR | 3.6 |
| 2 | 65.7 | 56.0 | 3.2 |
| 3 | 50.1 | 48.3 | 3.1 |
| 4 | 61.0 | NR | 7.1 |
| 5 | 38.0 | 37.0 | 3.5 |
| 6 | 39.9 | NR | 3.0 |
| 7 | 7.8 | 6.2 | 2.4 |
| 8 | 22.3 | 21.4 | 3.4 |

*Weight (gm)
NR = Not Reported

The indicated quantities of lipid cake were combined with approximately 21 ml of an organic solvent comprising chloroform and methanol (2:1, v/v) in an Eberbach 8575 microblender and homogenized for two minutes. The lipid/organic solvent homogenate was then centrifuged at 200 times gravity in a clinical centrifuge at room temperature for ten minutes to yield a clear, golden colored, supernatant and a particulate matter precipitant. The supernatant was isolated using conventional procedures and subjected to rotary evaporation at 37° C. under vacuum to completely remove the chloroform/methanol solvent. Other methods for solvent removal are known in the art and may be used in place of rotary evaporation. A viscous liquid was obtained which was then preferably suspended in approximately 4 ml of pBS for use.

The angiogenic activity of the extracted aqueous suspended lipid preparations were tested in the following manner: a series of New Zealand white rabbits were anesthetized with intravenous pentobarbitol (30 mg/Kg). From each preparation shown in Table I a single 50 microliter (hereinafter "$\mu l$") injection of the aqueous lipid suspension was made through a 25 gauge needle placed intrastromally into the cornea of each eye. The corneas of the animals were examined grossly and with an operating microscope on the second, fourth, sixth, eighth, and tenth day following ocular injection. Blood vessel growth and the presence of any corneal edema and/or inflammation was noted. On the tenth day after examination visually, the rabbits were individually sacrificed and histological slides, stained with hematoxylin and eosin in the conventional manner, were obtained from six micrometer thick sections cut from the formalin fixed enucleated eyes.

The angiogenic response was graded as follows: 0, identified no angiogenesis and a clear cornea; 1+, identified dilation of scleral vessels with red coloration noted at the limbus; 2+, identified several individual blood vessels migrating from the limbus two thirds of the way to the injection site; 3+, identified multiple blood vessels extending from the limbus to the injection site involving 10-20% of the cornea; 4+, identifies dense blood vessel formation extending from the limbus to the injection site involving at least 30-40% of the cornea.

For comparison purposes, an aqueous suspension of the omental lipid cake and an aqueous preparation of the subcutaneous non-omental fat were also prepared and tested. The non-omental fat preparation was made by combining a three gram portion of the fatty subcutaneous tissue with 4 ml of PBS and homogenizing this mixture using the Eberbach microblender for two minutes at 4° C. Similarly, an aqueous suspension of the omental lipid cake was prepared by homogenizing four gram portions of the lipid cake with 4 ml of PBS in the microblender for two minutes at 4° C. The homogenate of the whole omentum prior to centrifugation into proteinaceous fractions and lipid fractions was also evaluated. The results are as shown in Table II below.

TABLE II

| Test Sample | Angiogenic Activity (per 50 $\mu l$) |
|---|---|
| Extracted lipid preparation in aqueous medium | |
| No. 1 | 4+ |
| No. 2 | 4+ |
| No. 3 | 3+ |
| No. 4 | 4+ |
| No. 5 | 3+ |
| No. 6 | 4+ |
| No. 7 | 4+ |
| No. 8 | 4+ |
| PBS homogenate of lipid cake | |
| No. 1 | +1 |
| No. 2 | +1 |
| No. 3 | +1 |
| PBS homogenate of whole omentum | |
| No. 1 | +1 |
| No. 2 | +1 |
| No. 3 | +1 |
| PBS homogenate of non-omental fatty tissue | |
| No. 1 | 0 (inflammation) |
| No. 2 | 0 (inflammation) |
| No. 3 | 0 (inflammation) |
| PBS alone | |
| No. 1 | 0 |
| No. 2 | 0 |
| No. 3 | 0 |

The data indicates that excellent angiogenic activity was observed after a single 50 $\mu l$ central corneal injection of the chloroform/methanol lipid extract. In comparison, only minimal angiogenic activity was noted with the PBS homogenate of the total omentum and with the PBS homogenate of the lipid cake prior to extraction. No angiogenesis at all occurred in those instances following injection of PBS alone or the subcutaneous non-omental fat PBS homogenate. A complication however, noted in the data of Table II, was that the injected subcutaneous fat taken from the cat abdominal wall caused severe inflammation of the cornea within two days after corneal injection.

Figure 2:
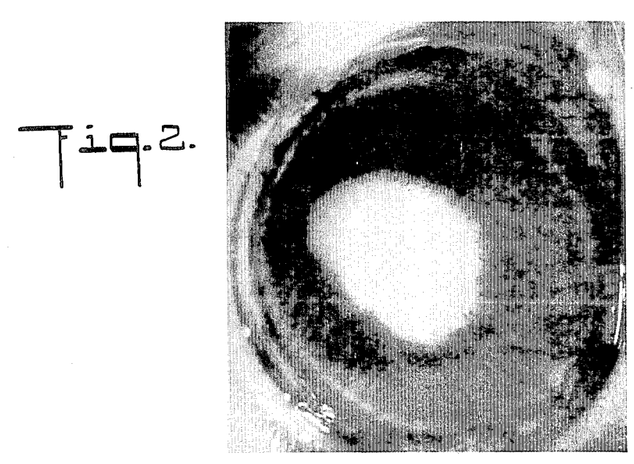
FIG. 2 is a photograph showing new blood vessel formation grossly in the corneas ten days after injection.
Figure 3:
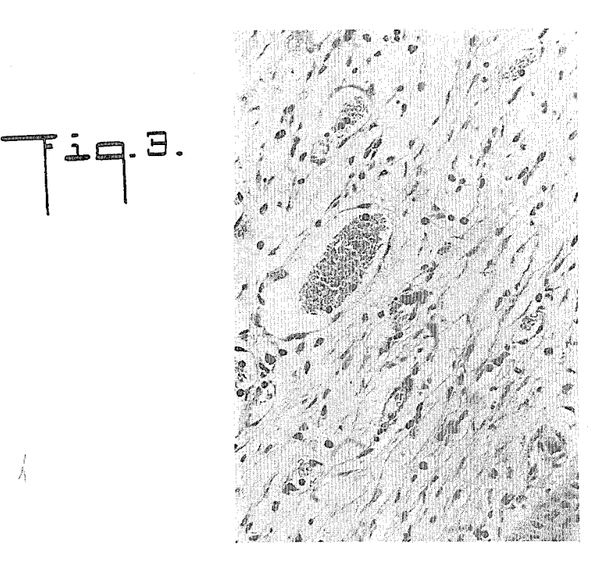
FIG. 3 is a photograph of a histological slide showing the microscopic formation of new blood vessels in the cornea after ten days.

The course of the angiogenic response in the cornea to the injected aqueous suspended chloroform/methanol lipid preparation followed a consistent pattern of rapid development and intense activity. Following injection of the extracted lipid fraction, a mild corneal inflammatory reaction was observed within twenty-four hours which subsided within forty-eight hours. This initial inflammation is characterized by slight clouding of the cornea with minimal erythema in the scleral area which was often accompanied with a slight discharge from the eye. A pannus, the appearance of a curtain of blood vessels around the margin of the cornea, with interstitial blood vessel formation became grossly evident 3 to 4 days following the injection. By the seventh to tenth day, the blood vessels had formed a dense and richly structured network within the cornea. This is illustrated by the photograph in FIG. 2. Histological examination of the enucleated eyes harvested on the tenth day showed multiple capillaries within the corneal stroma; a photograph of the histological section illustrating such multiple capillaries within the stroma is shown in FIG. 3.

It is of particular note that the solvent extracted lipid fraction in aqueous medium initiates and sustains angiogenesis after only a single 50 μl dose injection. Although the mechanism of this angiogenic process and response is presently unknown, it is apparent that the injection of the extracted lipid fraction from the omentum initiates and develops new blood vessel formation which becomes organized into dense, well structured, vascular networks in seven to ten days.

A second experiment was performed to demonstrate the neovascularization effects of the non-aqueous lipid preparation at a site where the normal vascularization in the tissue was purposely destroyed. Adult female cats were anesthetized with an intramuscular injection of Ketamine using a dosage of 7 ml/Kg. Each cat was placed in a supine position and an incision made between the knee and the inguinal crease of both hind legs. The femoral arteries were isolated, ligated, and removed between the groin and the first deep femoral branch (Hunter's canal). The incision was closed and each cat subjected immediately to an intravenous injection of stannous chloride/Technicium-99 which attaches to and radioactively labels the red blood cells in the tissue. The location and quantity of this radionuclide can be identified using a Gamma camera scan. In this manner, blood vessels and capillaries carrying the radioactively tagged red blood cells are specifically visualized.

The stanneous chloride/phosphate preparation was commercially obtained from New England Nuclear Company under the trade name "Pyrolite" and contained 10 mg of sodium pyrophosphate, 30 mg of sodium trimetaphosphate, and 0.95 mg stannous chloride. This preparation was reconstituted by adding 2.0 ml of PBS and 1.0 ml of this solution was injected intravenously into the bronchial vein of the cat. Twenty minutes later, an intravenous dose of 10 m Curries of Technesium-99 m was injected to radiolabel the red blood cells in that tissue area. Nuclear imaging scanning and digital integration of blood flow was observed and followed using a DTS-1600 ADAC Laboratory instrument coupled to a physiological synchronizer, model RC3000, obtained from Brattle Instruments.

After the cats had been surgically prepared, a "baseline" scan for background radioactivity of the surgical sites was made, followed by injection of between 6-7 ml of the chloroform/methanol extracted and evaporated viscous liquid lipid intramuscularly in equal amounts into two preselected and marked sites on the right leg in the area where the femoral artery was removed. A placebo injection containing only PBS was made into two similarly identified and marked sites on the left leg. Under normal circumstances, the recognized response of the body to this kind of surgery will be to try and establish collateral blood circulation to the injured tissues by forming new capillaries and blood vessels in the area where the femoral artery was severed. By following and comparing the rate and degree of new blood circulation in each leg following the surgery, a direct and verifiable assessment of the angiogenic properties and potency of the chloroform/methanol extracted lipid preparation was accurately made.

Figure 4A:
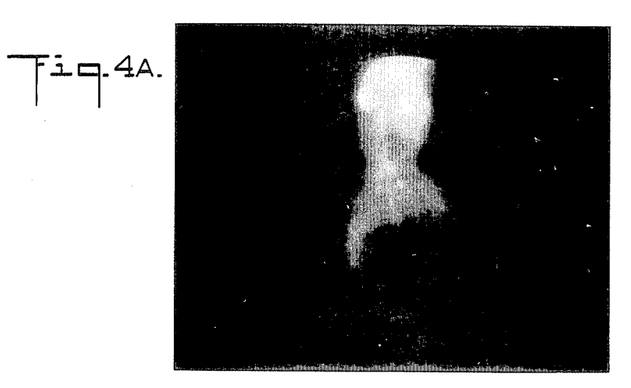
FIG. 4 are photographs of the Gamma camera scans of the right and left legs of a cat three days after surgery and omental lipid injection.
Figure 4B:
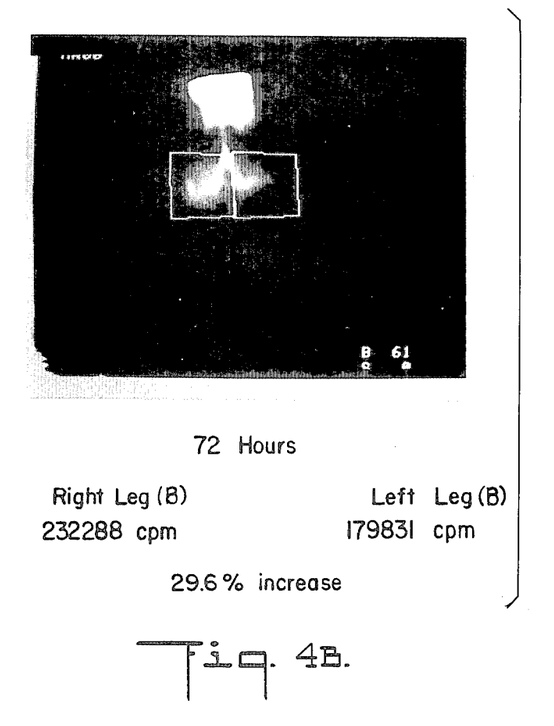
Figure 5:
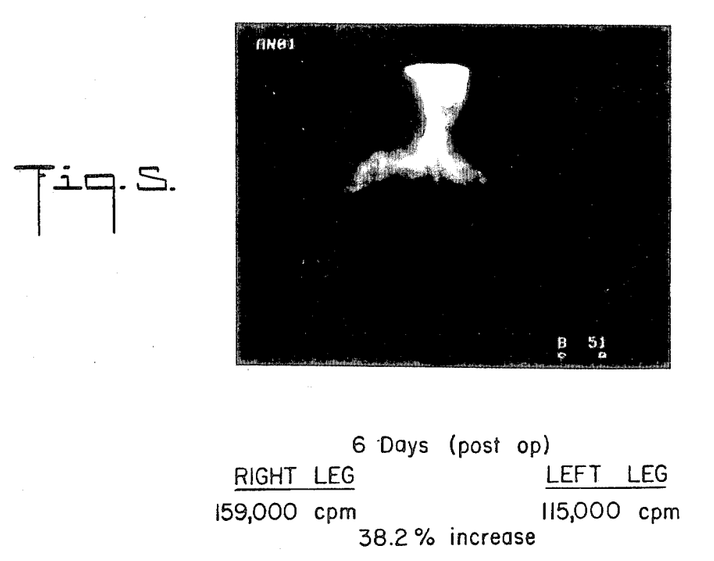
FIG. 5 are photographs of the Gamma camera scan of the right and left legs of a cat six days after surgery and omental lipid injection.
Figure 6:
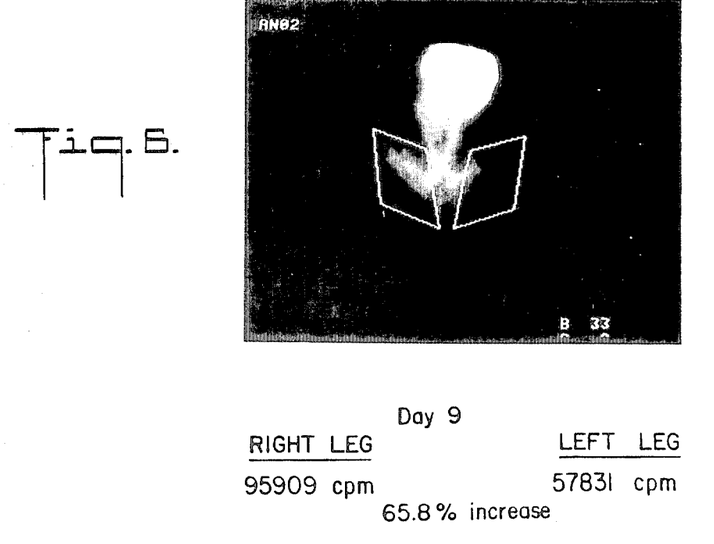
FIG. 6 is a photograph of the Gamma camera scan of the right and left legs of a cat nine days after surgery and omental lipid injection.
Figure 7:
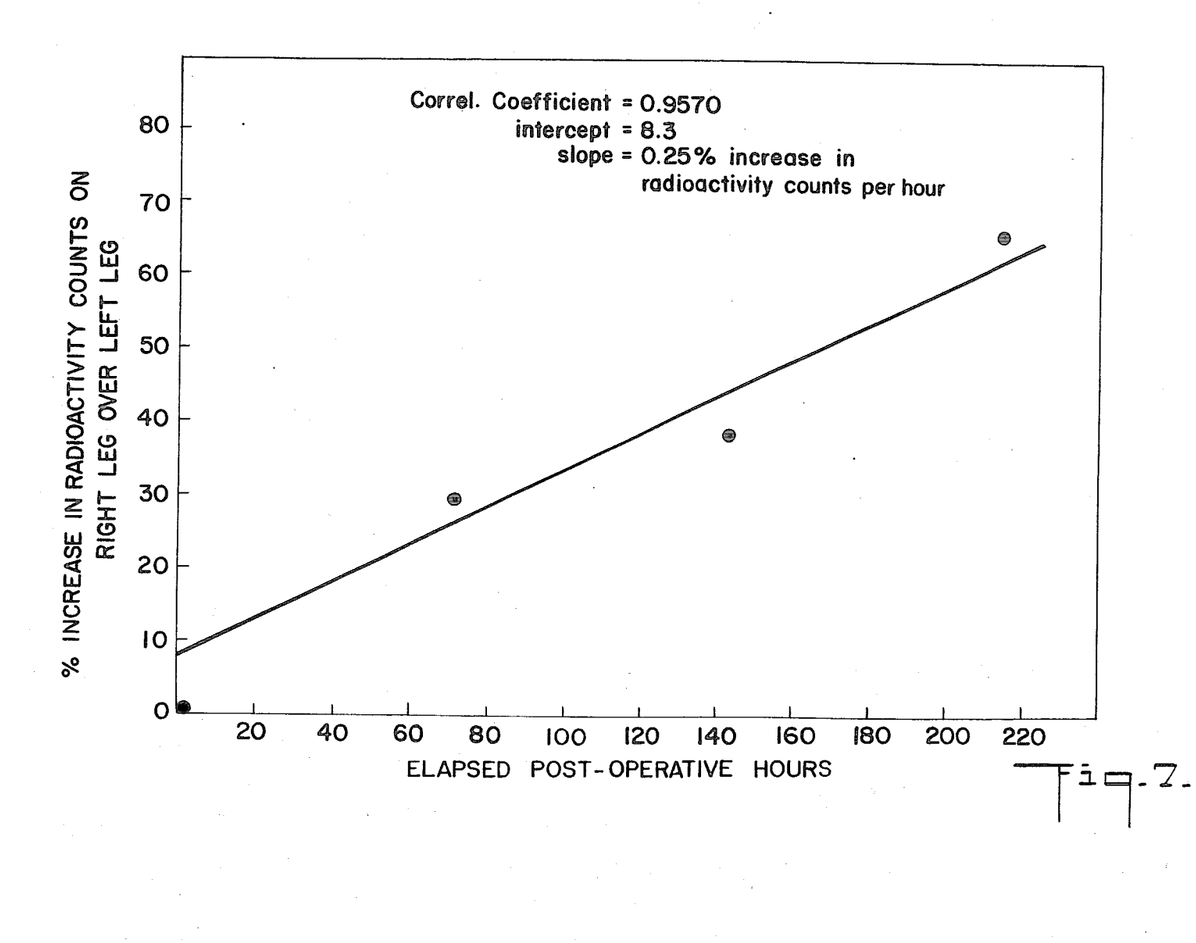
FIG. 7 is a graph illustrating the increase in neovascularization in the right leg of a cat after omental lipid injection as a function of time.

Subsequent intravenous injection of the stannous chloride/Technicium-99 m preparation was made into the preselected sites on each leg and each leg was subjected to nuclear scan at three, six, and nine days after the operation. The results of these nuclear scans are shown in FIGS. 4-6 which exemplify the effects of the lipid fraction for neovascularization in a representative cat. The data shows that the increase in blood vessel formation in the right leg of this cat (injected with the omental lipid preparation) had substantially higher integrated radioactivity counts then the left (control) leg. At seventy-two hours post surgery, a 29.6% difference in radioactivity was observed; at six days post operative time, a 38.2% increase in radioactivity was observed in the right leg in comparison to the left; and after nine days the rate of neovascularization in the right leg showed a 65.8% increase over that in the left leg. The photographs of FIGS. 4-6 provide visual evidence of the substantial differences in new blood vessel formation using the chloroform/methanol extracted lipid fraction. A graph illustrating a linear increase of radioactivity (in counts) comparing the lipid injected leg vascularization to the vascularization of the saline injected leg is provided in FIG. 7. The data reveals a rate of 0.25% per hour increase of neovascularization in the right leg compared to the left. This clearly shows the angiogenic effect of the lipid fraction as evidenced by the substantial increase in new blood vessel formation and vascular organization and structure in the right leg. This data however, overlooks the possibility of a common systemic effect by using the lipid extract preparation which was shown to be in effect by the following additional control experiment.

Figure 8:
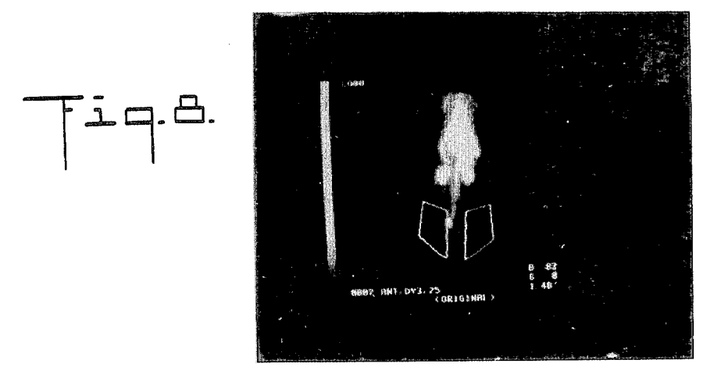
FIG. 8 is a photograph of a Gamma camera scan showing the vascularization in a cat recovering from surgery without the use of the angiogenic composition.
Figure 9:
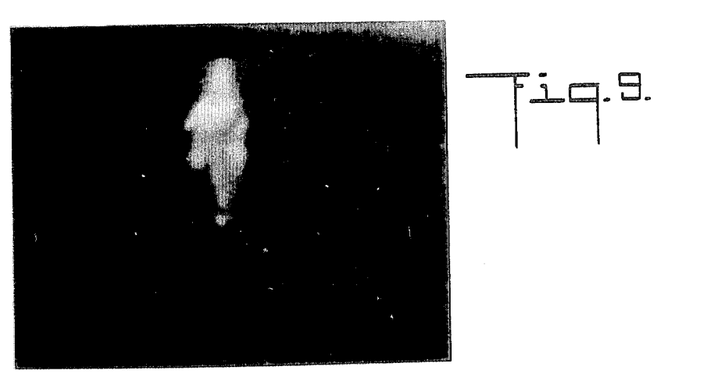
FIG. 9 is a photograph of a Gamma camera scan showing the anterior view of a leg of the cat in FIG. 8.
Figure 10:
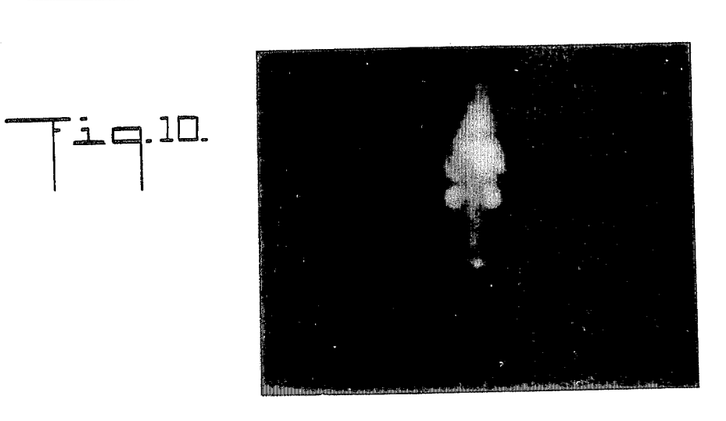
FIG. 10 is a photograph of the Gamma camera scan showing the posterior view of a leg of the cat in FIG. 8.

In this additional control, another cat was surgically operated upon to remove the femoral arteries as described above. But, in this instance, no injection of any kind was given. Gamma camera scans made at three and six day intervals post operatively are shown in FIGS. 8-10. The scan of the right and the left leg is shown in FIG. 8 in which no desirable difference in new blood vessel collateral circulation is visible after three days duration. FIG. 9 shows an anterior view of one leg on the sixth day post surgery and FIG. 10 shows the posterior view on the same day. The scans indicated no difference in counts between the two legs at any time post surgery and a much lesser degree of neovascularization in comparison to the earlier experiment. In fact, the neovascularization was noticeably less in this additional experiment than in the left (control) leg in the earlier work. In view of this and the fact that in the previous experiment that the left leg of the cat (injected control) exhibited a relatively higher degree of neovascularization (although substantially lesser than in the right leg), there is a basis for believing that part of the lipid preparation in the right leg was probably transferred systemically to the left leg in the earlier experiments.

In all these examples, the method for making the lipid preparation utilized the chloroform/methanol organic solvent of FIG. 1 for the extraction process. Although this is the preferred organic solvent for lipid extraction, other organic solvents are equally useful. These include chloroform/methanol in 1:1 ratios; chloroform/methanol/1NHCL in 4:2:3 ratios; tissue acidification using 1N HCL followed by two extractions of chloroform/ethanol in 1:2 ratios followed by methanol extraction; and a chloroform/methanol solvent in 1:2 ratios followed by a second extraction of methanol alone. Other organic solvents well characterized and known in the art may also be used to extract the lipid fraction from the omentum homogenate. These include ethyl ether, methylene chloride, methyl isobutyl ketone, and tetrahydrofuran; their usefulness as organic solvents however, must be correlated with their toxic and inflammatory residual properties, if any, when the extract after solvent removal is introduced into the living tissues. Additional solvents, regardless of their polarity, their strength, their solubility, their viscosity, or any other physical properties are also believed to be useful for the extraction process provided the solvent is subsequently removed and there are no residual biological effects on the lipid extract.

Figure 11:
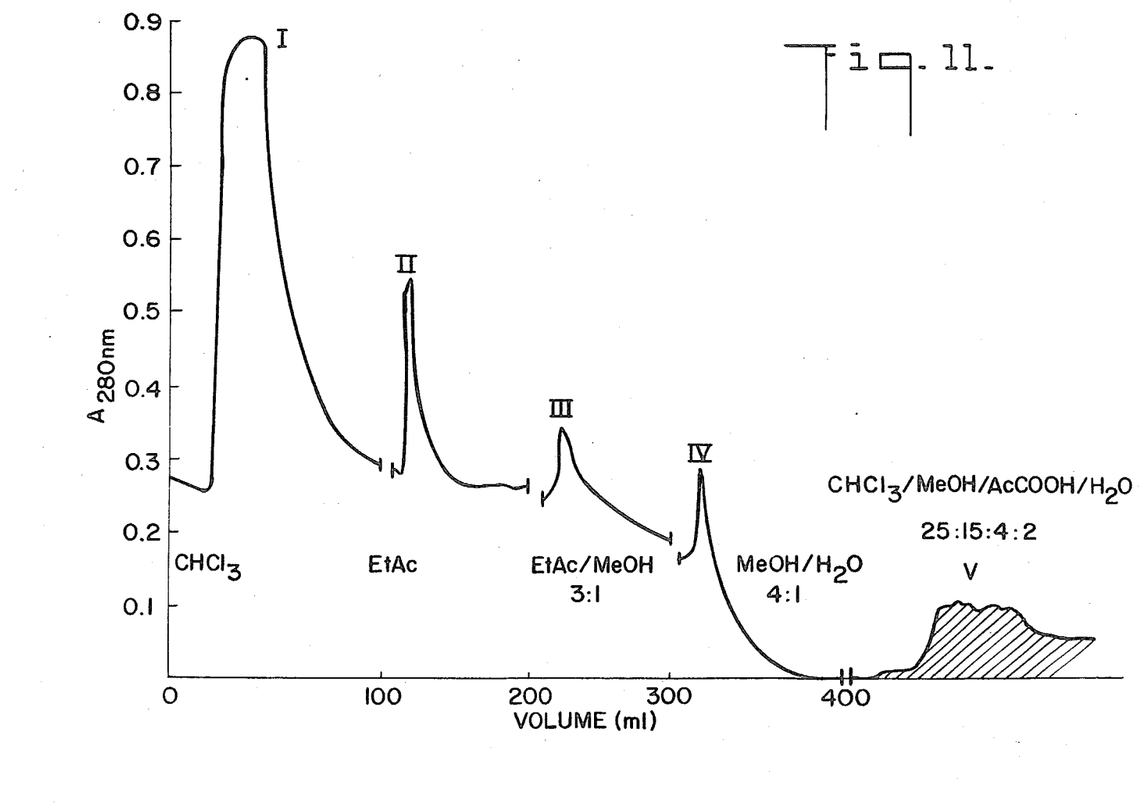
FIG. 11 is a graph illustrating the elution of subfractions I-V comprising the extracted lipid preparation.

The chloroform/methanol (2:1 v/v) lipid extract illustrated in FIG. 1 was further characterized as to its component parts or subfractions using liquid chromatography. For these chromatographic fractionations the procedures described in A. Kuksin, *Chromatography Part B'* (E. Heftmann, editor), Elsevier, New York, 1983, were used. In our method, 5.0 ml of the chloroform/methanol lipid extract was placed in a chromatography column containing silica gel (100-200 mesh Sigma Chemical Company) which was previously equilibrated with chloroform. Other chromatographic packings useful for fractionation include silicic acid columns, DEAE-cellulose columns, and Sephadex LH-20 columns. Using the silica gel columns, elutions was performed in sequence using 100 ml aliquots of the following solvents: chloroform; ethyl acetate; ethyl acetate/methanol (3:1); methanol/water (4:1) followed by 200 ml of a solvent mixture comprising chloroform/methanol/acetic acid/water (25:15:4:2). The individual elution fractions were obtained and measured using ultraviolet light at 280 nanometers. The results are illustrated in FIG. 11 in graphic form and identify the recovery of subfractions I–V individually. Subsequent testing of each of these lipid subfractions, showed angiogenic activity to be present only in subfraction V with no noticeable angiogenic effect from any of the subfractions I–V. The overall activity of subfraction V however, was measurably less than the chloroform/methanol lipid extraction preparation originally obtained. It was subsequently found that subfactors I–IV, although having no angiogenic activity in and of themselves, when combined with subfraction V act to enhance and increase the activity and potency of the angiogenic composition as a whole.

The chloroform/methanol lipid preparation comprising subfractions I–V was also subjected to preliminary mass spectrum analysis by means of the electron impact method which method, as is known in the art, only determines molecular weight ions in the low range to a maximum of 600. Further work is needed to determine higher molecular weight species. The results indicate that the extracted lipid preparation as a whole may comprise in part in the low molecular weight range a variety of lipid-like molecules in admixture ranging in molecular weight from approximately 150–1,100 daltons. It is believed that these lipid molecules themselves comprise a lipid fragment and one or more aliphatic hydrocarbon chains, each chain being preferably less than ten but possibly not more than twenty carbons in length and ranging in weight from 40–350 daltons. Furthermore, it is believed that some of these lipid molecules which have a molecular weight in the range from 350–600 daltons may combine to form molecular aggregates ranging in weight from 800–1,100 daltons. While the aggregates, lipid molecules and lipid fragments always comprise carbon, hydrogen and oxygen in combination, some molecular aggregates and lipid molecules comprise nitrogen and phosphorus as well. Each of the preparations analyzed and evaluated (the chloroform/methanol extracted aqueous lipid preparation and subfractions I–V) were shown to be heterogeneous in nature and to contain the above described variety of compositions. For these reasons, all lipid-like preparations derived from omentum which are extracted by at least one organic solvent and which show angiogenic activity upon introduction into living tissues are within the scope of the present invention.

The uses and applications of the present invention are therapeutic in situations when an increased number of capillaries or new blood vessel formation is clinically needed. The immediate uses include but are not limited to the following:

In burns and wound healing: Two major problems which immediately threatened the lives of severely burned patients are excessive fluid loss and massive infection. Current medical treatment involves fluid resuscitation and a prompt closure of wounds with skin autographs, transplantation of cadaver skin or pig skin. Other presently known procedures include the use of a bilateral polymeric membrane to asceptically closed skin burn wounds in human while serving as a template subsequently for the construction of new skin. During this time period, however, threatening infections frequently occur especially in patients with third degree burns. Incorporation of angiogenic compositions into artifical skin will facilitate the formation of new blood vessels in the healing wound and will therefore minimize the chances of infection.

Some fractures in the body, as in the low tibial region, are known for their tendency to delay in healing or for non-union of the fracture. The reason for this is the normally occurring decrease in blood supply at the lower part of the leg. The addition of an angiogenic factor between and surrounding a fracture site in such a location is expected to accelerate or even accomplish fracture healing.

In cardiovascular disease: A well recognized response to myocardial infarction is the long term repair of the cardiac tissue by the ingrowth of new blood vessels from the surrounding myocardium. The nature of the stimulus which induces angiogenesis in the heart under these conditions is presently not known. The use of the novel angiogenic compositions may prevent heart attack by increasing the blood circulation through new blood vessels to the anginal cardiac tissue before this tissue becomes infarcted. Treatment with the novel angiogenic composition and methodology will also speed up recovery after myocardial infarction and also will be beneficial to patients with coronary occlusions with or without angina.

With stroke: Cerebral arterial insufficiency causes stroke in approximately half a million new patients per year in the U.S. alone. Similarly, transient ischemic attacks, defined as episodes of neurological dysfunction followed by recovery within twenty-four hours, occurs in up to 50% of patients prior to having a major stroke. Introduction of the present angiogenic composition will improve vascularization in the cerebrum, reduce the risk of transient ischemic attacks substantially, and be used as a therapeutic approach over time for the treatment of such patients.

In peripheral vascular disease: The blood flow in the extremities, legs and arms, is often diminished in the patient due to age, disease, surgery, and trauma. The introduction of the angiogenic composition described herein will increase the blood flow in the extremities and create new vascularization, blood vessels and capillaries, in the extremities to increase the blood flow in its most needed areas.

The invention therefore is not to be restricted in form nor limited in scope except by the claims appended hereto.

What is claimed is:

1. A partially purified essentially non-protein angiogenic composition obtained from mammalian omenta by extraction with a solvent comprising at least one organic solvent and characterized by being a heterogeneous lipid containing fraction possessing systemic angiogenic or blood flow enhancement activity for mammalian tissues or organs wherein the systemic activity targets to a damaged, insufficient or abnormal vascular component of the mammalian tissue or organ.

2. The composition of claim 1 wherein the solvent is chloroform-methane.

3. The composition of claim 1 wherein angiogenic activity is determined according to the rabbit cornea test.

4. The composition of claim 1 wherein systemic targeting angiogenic or blood flow enhancement activity is determined according to a radioactive cat leg neovascularization test.

5. The composition comprising the active subfraction of claim 1.

6. The active subfraction of claim 5 in combination with the inactive fraction obtained when mammalian omenta is extracted with at least one organic solvent and wherein systemic targeting of angiogenic or blood flow enhancement activity is improved.

7. The angiogenically active composition of claims 1, 5, 6 for angiogenic or blood flow enhancement formulated for maintenance of mammalian organs or tissues in culture, or healing of, or acceleration of healing of: wounds, ulcers, muscle tissue, burns, bone fractures or breaks, myocardial infarcts, damage due to strokes, cerebral arterial insufficiency, coronary occlusions, restricted blood flow, damaged blood vessels, or diminished blood flow to extremities.

8. Method for neovascularization or blood flow enhancement of mammalian tissue which comprises treating a mammalian subject with vascular damage or insufficiency with the angiogenic composition of claim 1.

9. Method of claim 8 wherein the neovascularization or blood flow enhancement of mammalian tissues comprises maintenance of mammalian tissues or organs in culture, or healing of, or acceleration of healing of: wounds, ulcers, muscle tissue, burns, bone fractures or breaks, myocardial infarcts, damage due to strokes, cerebral arterial insufficiency, coronary occlusions, restricted blood flow, damaged blood vessels, or diminished blood flow to extremities.

10. Method for obtaining a composition active in systemic targeting angiogenesis or blood flow enhancement from mammalian omenta which comprises:
   (a) separating an omental homogenate into several layers which comprise a protein-containing layer and a lipid-enriched layer, and
   (b) extracting the omental lipid-enriched layer with a solvent comprising at least one organic solvent wherein there is obtained an essentially non-protein lipid fraction active in systemic targeting angiogenesis or blood flow enhancement.

* * * * *

UNITED STATES PATENT AND TRADEMARK OFFICE
CERTIFICATE OF CORRECTION

PATENT NO.   :   4,699,788

DATED        :   October 13, 1987

INVENTOR(S)  :   Nicholas Catsimpoolas

It is certified that error appears in the above-identified patent and that said Letters Patent is hereby corrected as shown below:

Column 2, line 48:    first word, delete "29" and insert -- 129 --.

Column 4, line 15:    first word, after "(" delete "hereinaiter" and insert -- hereinafter --.

Column 11, line 17:    after "chloroform-" delete "methane" and insert -- methanol --.

Signed and Sealed this

Seventh Day of June, 1988

Attest:

DONALD J. QUIGG

Attesting Officer    Commissioner of Patents and Trademarks